(12) United States Patent
Zalis et al.

(10) Patent No.: US 9,299,156 B2
(45) Date of Patent: Mar. 29, 2016

(54) STRUCTURE-ANALYSIS SYSTEM, METHOD, SOFTWARE ARRANGEMENT AND COMPUTER-ACCESSIBLE MEDIUM FOR DIGITAL CLEANSING OF COMPUTED TOMOGRAPHY COLONOGRAPHY IMAGES

(75) Inventors: Michael Zalis, Newtonville, MA (US); Wenli Cai, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 2090 days.

(21) Appl. No.: 12/089,662

(22) PCT Filed: Oct. 17, 2006

(86) PCT No.: PCT/US2006/060038
§ 371 (c)(1),
(2), (4) Date: Nov. 20, 2008

(87) PCT Pub. No.: WO2007/048091
PCT Pub. Date: Apr. 26, 2007

(65) Prior Publication Data
US 2009/0304248 A1 Dec. 10, 2009

Related U.S. Application Data

(60) Provisional application No. 60/727,946, filed on Oct. 17, 2005.

(51) Int. Cl.
G06T 7/00 (2006.01)
G06F 19/00 (2011.01)
G06T 5/00 (2006.01)

(52) U.S. Cl.
CPC ............ *G06T 7/0083* (2013.01); *G06F 19/321* (2013.01); *G06F 19/3437* (2013.01);
(Continued)

(58) Field of Classification Search
USPC .................. 324/300–322; 382/128–131; 600/407–435; 348/65
See application file for complete search history.

(56) References Cited

U.S. PATENT DOCUMENTS

| 6,331,116 | B1 | 12/2001 | Kaufman |
| 6,477,401 | B1 | 11/2002 | Johnson et al. |

(Continued)

FOREIGN PATENT DOCUMENTS

| KR | 2002-0041577 | 6/2002 |
| WO | WO 98/37517 | 8/1998 |

(Continued)

OTHER PUBLICATIONS

European Supplementary Search Report issued Nov. 11, 2011 for European Patent Application No. 06839454.

(Continued)

*Primary Examiner* — Melissa Koval
*Assistant Examiner* — Tiffany Fetzner
(74) *Attorney, Agent, or Firm* — Andrews Kurth LLP

(57) ABSTRACT

A system, method, software arrangement and computer-accessible medium for performing electronic cleansing of CT colonography images are provided. In this system, method, software arrangement and computer-accessible medium, the digital bowel cleansing can be performed to remove tagged bowel contents from the images. The digital bowel cleansing can apply a local shape analysis throughout the images and use a shape-based speed function to detect the folds and polyps structures while removing the tagged bowel contents region. The system, method, software arrangement and computer-accessible medium can enable a medical examiner to perform an accurate virtual colonoscopy on a patient, without the need for thorough patient preparation.

51 Claims, 14 Drawing Sheets

(52) U.S. Cl.
CPC ............... *G06T5/005* (2013.01); *G06T 7/0089* (2013.01); *G06T 7/0091* (2013.01); *G06T 2207/10081* (2013.01); *G06T 2207/20161* (2013.01); *G06T 2207/30032* (2013.01)

(56) References Cited

U.S. PATENT DOCUMENTS

| | | | |
|---|---|---|---|
| 6,514,082 | B2 | 2/2003 | Kaufman et al. |
| 6,947,784 | B2 | 9/2005 | Zalis |
| 2002/0097320 | A1 | 7/2002 | Zalis |
| 2005/0107691 | A1 | 5/2005 | Zalis |
| 2005/0152588 | A1* | 7/2005 | Yoshida et al. ............... 382/128 |
| 2009/0005693 | A1* | 1/2009 | Brauner et al. ............... 600/481 |
| 2009/0304248 | A1* | 12/2009 | Zalis et al. ................... 382/131 |
| 2010/0260390 | A1* | 10/2010 | Liang et al. ................... 382/128 |

FOREIGN PATENT DOCUMENTS

| | | |
|---|---|---|
| WO | WO 2005/036457 | 4/2005 |
| WO | WO 2005036457 A2 * | 4/2005 |

OTHER PUBLICATIONS

Second Office Action for Canadian Patent Application No. 2,626,040 dated Feb. 23, 2015.
Examination Search Report for Canadian Patent Application No. 2,626,040 dated Aug. 12, 2014.
Office Communication for European Patent Application No. 06839454.3 dated Jul. 13, 2015.

* cited by examiner

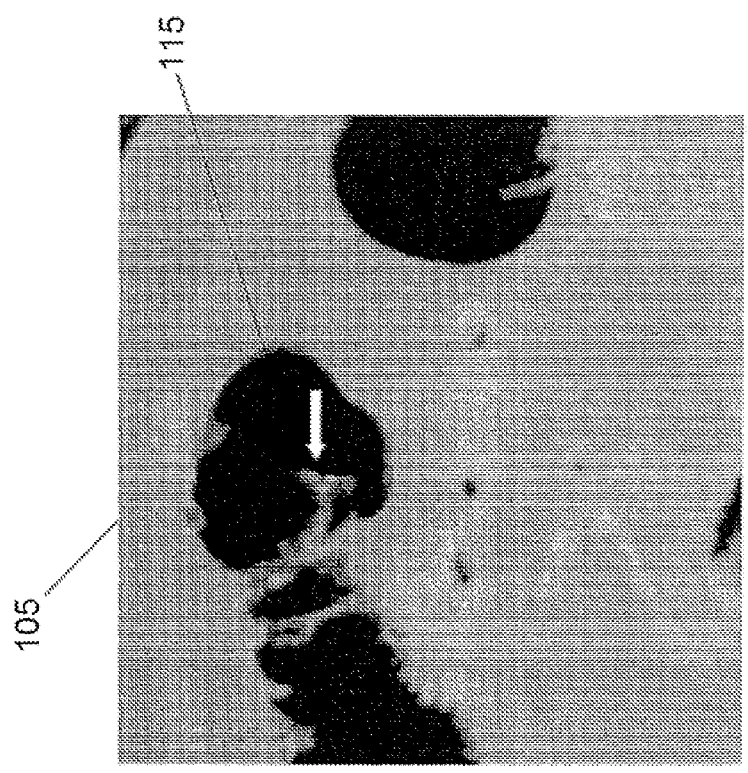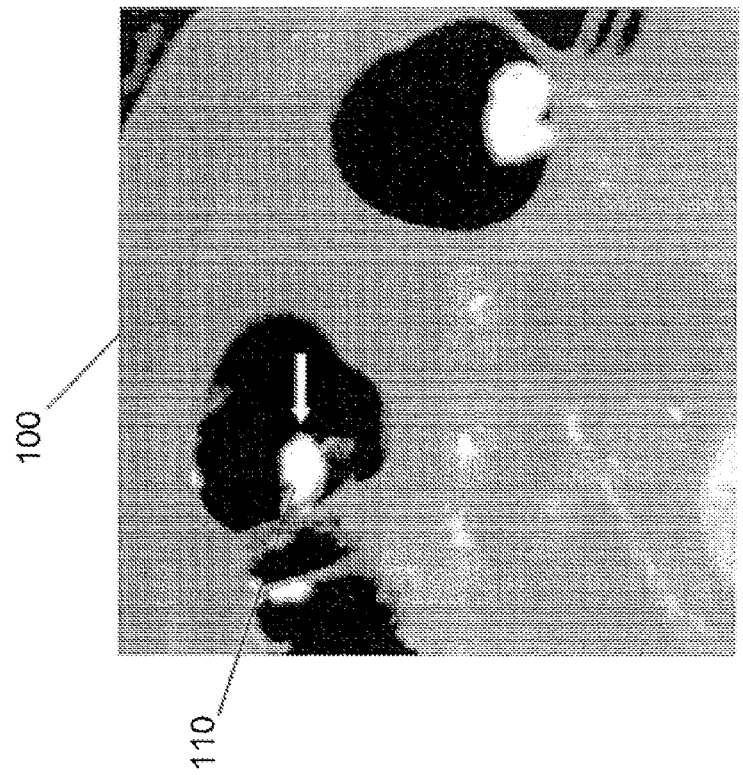
FIG. 1 (PRIOR ART)

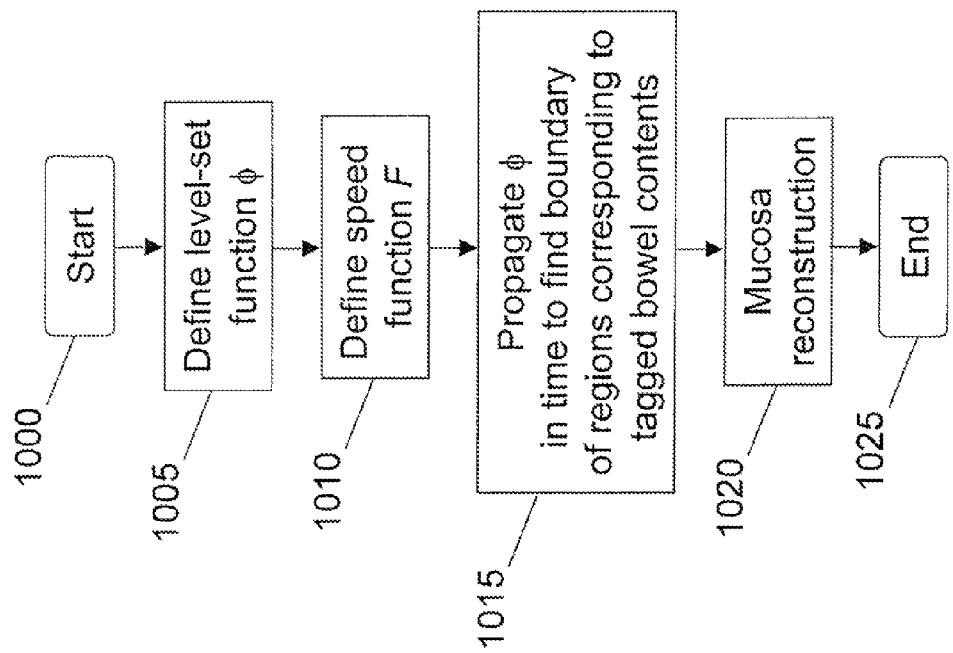

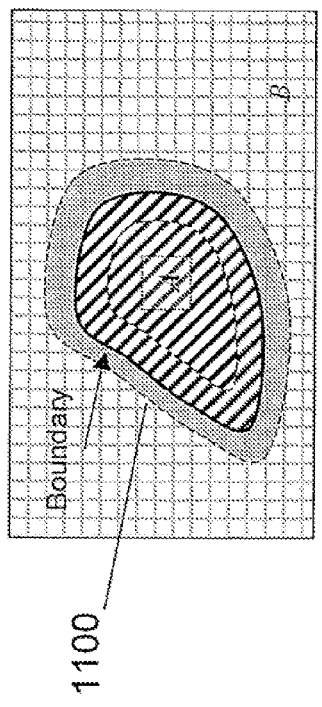
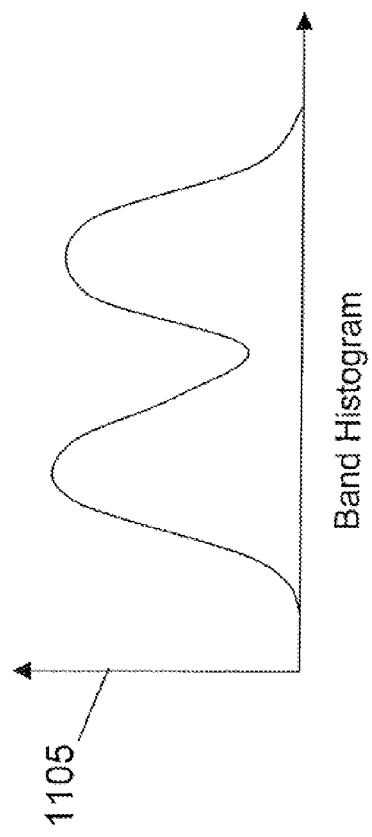
FIG. 11A
FIG. 11B

STRUCTURE-ANALYSIS SYSTEM, METHOD, SOFTWARE ARRANGEMENT AND COMPUTER-ACCESSIBLE MEDIUM FOR DIGITAL CLEANSING OF COMPUTED TOMOGRAPHY COLONOGRAPHY IMAGES

CROSS-REFERENCE TO RELATED APPLICATION

This application is based upon and claims the benefit of priority from U.S. Patent Application Ser. No. 60/727,946, filed Oct. 17, 2005, the entire disclosure of which is incorporated herein by reference.

STATEMENT OF FEDERAL SUPPORT

The present invention was made with U.S. Government support under grant number CA98422 from the National Institute of Health. Thus, the Government may have certain rights to the invention described and claimed herein.

FIELD OF THE INVENTION

The present invention relates generally to digital cleansing of computed tomography ("CT") colonography images. In particular, this invention relates to a system, method, software arrangement and computer-accessible medium which employ a structure-analysis method that uses the local shape signatures to electronically cleanse tagged bowel contents from the images.

BACKGROUND INFORMATION

It is known that colorectal cancer is the second most common cause of cancer deaths in the United States and Europe. Screening for colorectal cancer can result in a significant reduction in cancer mortality. The currently most popular exam for visualizing the colon is a colonoscopy, which is an invasive and painful exam. A colonoscopy may be performed to screen for colorectal cancer as well as a number of other colon pathologies, including Crohn's disease and irritable bowel syndrome. However, due to the nature of the exam, its screening recommendation is often ignored by the public at large.

As known to those skilled in the art, a colonoscopy generally refers to a medical procedure for examining a patient's colon to detect abnormalities such as polyps, tumors or inflammatory processes in the anatomy of the colon. The colonoscopy consists of a direct endoscopic examination of the colon with a flexible tubular structure known as a colonoscope, which has fiber optic or video recording capabilities at one end thereof. The colonoscope is inserted through the patient's anus and directed along the length of the colon, thereby permitting direct endoscopic visualization of colon polyps, e.g., abnormal growths in the colon, and tumors, and in some cases, providing a capability for endoscopic biopsy and polyp removal.

Although colonoscopy provides a precise way of colon examination, it is generally time-consuming, expensive to perform, and requires great care and skill by the medical examiner. In addition, such procedure may require a thorough patient preparation, including a ingestion of purgatives and enemas, and usually a moderate anesthesia. Since colonoscopy is an invasive procedure, there may likely be a significant risk of injury to the colon and the possibility of colon perforation and peritonitis, which can be fatal.

To overcome these drawbacks, the virtual colonoscopy procedure was developed. For example, a virtual colonoscopy makes use of images generated by computed tomography ("CT") imaging systems, which can also be referred to as computer assisted tomography ("CAT") imaging systems. In a CT or CAT imaging systems, a computing device may be used to produce an image of cross-sections of regions of the human body by using measure attenuation of X-rays through a cross-section of the body. In a virtual colonoscopy, the CT imaging system usually generates two-dimensional images of the internals of the intestine. A series of such two-dimensional images can be combined to provide a three-dimensional image of the colon.

While this CT or CAT procedure does not require an insertion of an endoscope into a patient and thus avoids the risk of injury to the colon and the possibility of colon perforation and peritonitis, such procedure still may require a thorough patient preparation, including the use of purgatives and enemas. Generally, the patient should stop eating, and purge the bowel by ingesting (typically by drinking) a relatively large amount of a purgative. Another problem with the virtual colonoscopy approach is that the accuracy of examinations and diagnosis using virtual colonoscopy techniques is not as accurate as is desired. This is due to, at least in part, the relatively large number of images the medical examiner (e.g., a doctor) should examine to determine if a polyp, tumor and/or an abnormality exists in the colon.

Recent advances in the virtual colonoscopy space have suggested that image processing techniques may be used to remove the need for bowel cleansing prior to the procedure. For example, U.S. Pat. No. 6,947,784 and U.S. Patent Publication No. 2005/0107691, the entire disclosures of which are incorporated herein by reference, describe a procedure in which bowel contents are tagged with contrast agents ingested by the patient and eliminating the tagged bowel contents with electronic cleansing ("EC") techniques.

The EC techniques disclosed in one or both of these publications involve a combination of thresholding and filtering techniques. An exemplary procedure provides that a global threshold is initially set to the tagged bowel contents. For example, the pixels in a CT image having an attenuation higher than the threshold are then subtracted from the image. Further, a smoothing filter may be used to average the abrupt transitions between the native and subtracted regions in the image.

Studies have shown that EC techniques increase the diagnostic ability of CT colonoscopy. See, for example, Pickart, P. and Choi, J., "Electronic Cleansing and Stool Tagging in CT Colonography: Advantages and Pitfalls with Primary Three-Dimensional Evaluation," Am. J. Roentgenol., Sep. 1, 2003, 181(3):799-805, the entire disclosure of which is incorporated herein by reference. However, the current EC techniques are limited in that they may not be capable of removing all of the bowel contents that are not a result of or associated with an abnormality.

In particular, current EC techniques may not be able to handle three types of artifacts that are visible in the CT images after EC is performed: (i) pseudo-polyps, (ii) under-cleansing artifacts, and (iii) degraded folds.

Pseudo-polyps may appear as true polyps, but they generally arise out of partial volume effects between air and tagged bowel contents. Current threshold-based methods may not cleanse bowel contents completely. For example, FIG. 1 shows that after a performance of an exemplary conventional EC procedure so as to cleanse the tagged bowel contents 110 in a CT image 100, a pseudo-polyp artifact 115 that remained in the CT image 105.

Under-cleansing artifacts generally arise due to the heterogeneity of the tagging contrast, which tends to result in low attenuation materials that may not be removed via thresholding. For example, FIG. 2 shows that after EC was performed to cleanse the tagged bowel contents 210 in the CT image 200, a heterogeneously opacified colonic contents 215 remained in the CT image 205.

Using the conventional EC procedures. degraded folds, which generally appear as haustral folds surrounded by tagged bowel contents, may be inappropriately removed or obscure mucosal polyps due to over-segmentation of the tagged bowel contents and potential pseudo-enhancement affecting these extremely thin structures. For example, FIG. 3 shows that after EC was performed to cleanse the tagged bowel contents 310 in CT image 300, the degraded folds 315 remained in the CT image 305. Due to a pseudo-enhancement, a part of the thin fold provided next to the bowel contents 310 was inappropriately removed, resulting in the degraded fold 315 in the CT image 305.

These artifacts appear visually distracting, therefore limiting the usefulness of the currently-available EC techniques for clinical interpretation of CT colonography images. To address these concerns, certain image processing techniques have been developed to remove the artifacts which remain after the EC procedure is performed.

For example, to address the partial volume effects that may result in pseudo-polyps and other artifacts, a technique was developed and disclosed in Chen, D., et al., "A Novel Approach to Extract Colon Lumen from CT Images for Virtual Colonoscopy," IEEE Trans. on Medical Imaging, Vol. 19, pp. 1220-26, 2000, the entire disclosure of which is incorporated herein by reference. The technique described in this publication involves Markov random field to characterize each voxel by its local feature vector.

To address the over-segmentation problem, Zalis et al., "Digital Subtraction Bowel Cleansing for CT Colonography Using Morphological and Linear Filtration Methods," IEEE Trans. on Medical Imaging, Vol. 23, pp. 1335-43, 2000, the entire disclosure of which is incorporated herein by reference, suggests using an edge filter to identify regions with artifacts and add the over-subtracted regions back before smoothing.

Both of these image processing techniques employ thresholding and region growing to segment tagged bowel contents. However, they still cannot solve the problems caused by the heterogeneity of the tagged bowel contents (shown in FIG. 2) and the problems caused by degraded folds (shown in FIG. 3).

There is a need to overcome the deficiencies described herein above.

OBJECTS AND SUMMARY OF THE INVENTION

In view of the foregoing, one of the objects of the present invention is to accurately detect polyps, tumors, and other abnormalities in the colon, while removing undesirable artifacts and reducing a need for an extensive and unpleasant patient preparation.

It is another object of the present invention to employ a local shape signature in the CT colonography images to electronically cleanse tagged bowel contents from these images.

It is yet another object of the present invention to combine the use of local shape signatures in the CT colonography images with a shape-based speed function in level-set segmentation to identify and remove tagged bowel contents from the images without affecting the accurate detection of polyps, tumors, and other abnormalities in the colon.

These and other objects of the present invention can be accomplished using an exemplary embodiment of the system, method, software arrangement and computer-accessible medium of a EC technique that employs a structure-analysis method that uses the local shape signatures in the CT colonography images to electronically cleanse tagged bowel contents from the images.

In accordance with the present invention, a system for performing a virtual colonoscopy may include a CT imaging system for generating CT colonography images, a storage device, e.g., a database, for storing the CT colonography images, and an EC processor ("ECP") coupled to receive the CT colonography images from the storage device and for processing the received images to electronically cleanse tagged bowel contents from the CT image. With this exemplary arrangement, a system which provides accurate detection of polyps, tumors, and other abnormalities in the colon may be provided, which does not require a thorough and extensive patient preparation.

In one exemplary embodiment of the present invention, the ECP receives image data from the image database and processes the image data to electronically cleanse the contents of the bowel from the images. The ECP can then store the image back into the image database. Since the ECP cleanses the bowel contents electronically, the patient undergoing the virtual colonoscopy need not purge the bowel in the conventional manner which is known to be unpleasant to the patient.

In yet another exemplary embodiment of the present invention, an exemplary EC technique implemented in the ECP may be used for electronically cleansing of CT colonography images. This exemplary EC technique may include: (i) initial segmentation of the colon in the images, (ii) initial classification of the segmented colon in the images, (iii) computation of local-shape signatures in the images; (iv) detection of soft-tissue structures (polyp and fold) while subtracting the tagging regions in the images, and (v) mucosa reconstruction.

The initial segmentation step can segment the colon from its background in the CT images. The segmented colon includes (i) colonic wall, (ii) colonic lumen, and (iii) tagged bowel contents. The initial classification step can follow the initial segmentation step to classify the segmented CT images into a number (e.g., three) different materials: (i) air, (ii) soft tissues, and (iii) tagged bowel contents. Both the initial segmentation step and the initial classification step may be performed using a combination of conventional image processing techniques, including thresholding, connectivity, morphological operation, and use of texture features, such as standard deviation, local histogram, entropy, and energy, among others.

The computation of local shape signatures in the CT images may be performed by using the eigenvalues of a Hessian operator applied to the segmented CT images to improve identification and preservation of folds and polyps submerged in the tagging regions. The structure cleansing procedure may employ a shape-based speed function based on the local shape signatures in the images to correctly identify the boundary and contour of surfaces in the colon so that the tagged bowel contents can be accurately removed. The mucosa reconstruction step may then be applied to replace the accurately removed tagged bowel contents with air and reconstruct the colonic walls.

According to another exemplary embodiment of the present invention, an automated polyp detection processor ("APDP") can be provided to receive images from the database and for processing the received images to detect polyps, tumors, and other abnormalities in the colon. The APDP can thus pre-screen each image in the database such that a medical examiner, e.g., a doctor, need not examine every image, but rather, can focus attention on a subset of the images possibly having polyps or other irregularities. Since the exemplary embodiments of the present invention may generate a relatively large number of images for each patient undergoing the virtual colonoscopy, a medical examiner may be availed more time to focus on those images in which it is most likely to detect a polyp or other irregularity in the colon. The APDP can process images which have been generated using either conventional virtual colonoscopy techniques, e.g., techniques in which the patient purges the bowel prior to the CT scan, or the APDP can process images in which the bowel contents have been electronically cleansed, e.g., images which have been processed by the ECP and stored back into the database.

Advantageously, because tagged bowel contents are accurately removed from CT colonography images in accordance with the present invention, virtual colonoscopy exams may be easily performed on patients without the need for thorough patient preparation.

BRIEF DESCRIPTION OF THE DRAWINGS

The foregoing and other objects of the present invention will be apparent upon consideration of the following detailed description, taken in conjunction with the accompanying drawings, in which like reference characters refer to like parts throughout, and in which:

FIG. 1 shows exemplary CT colonography images resulting from a use of conventional EC techniques to electronically cleanse tagged bowel contents from the images;

FIG. 10 shows a flow diagram of an exemplary embodiment of a procedure according to the present invention for performing a structure-analysis EC using a local shape signatures from the CT colonography images;

FIG. 11A shows an illustration of an exemplary moving band around an object boundary formed using an exemplary dynamic histogram analysis in accordance with the present invention;

FIG. 11B shows a graph of an exemplary band histogram generated using the dynamic histogram analysis in accordance with the present invention;

DETAILED DESCRIPTION OF EMBODIMENTS OF THE INVENTION

Generally, in accordance with exemplary embodiments of the present invention, a system, method, software arrangement and computer-accessible medium are provided for EC of the CT colonography images that combines the use of structure-analysis in the images with a local shape signature to identify and remove tagged bowel contents from the images without affecting the accurate detection of polyps, tumors, and other abnormalities in the colon. As described herein, EC generally refers to a removal of tagged bowel contents and other artifacts from CT colonography images during a virtual colonoscopy. The designed shape-based speed function in level set generally acts on a particular colon surface and at any moment in time, defines a "level-set" partial differential equation ("PDE") which is solved to determine the surface position. The shape-based speed function may be applied to determine the contour and boundary of surface regions in the colon corresponding to tagged bowel contents so they can be accurately removed from the CT colonography images. As understood by those of ordinary skill in the art, the principles and embodiments of the present invention may be clearly used to perform virtual colonoscopy examinations on patients without the need for a thorough patient preparation.

Figure 2:
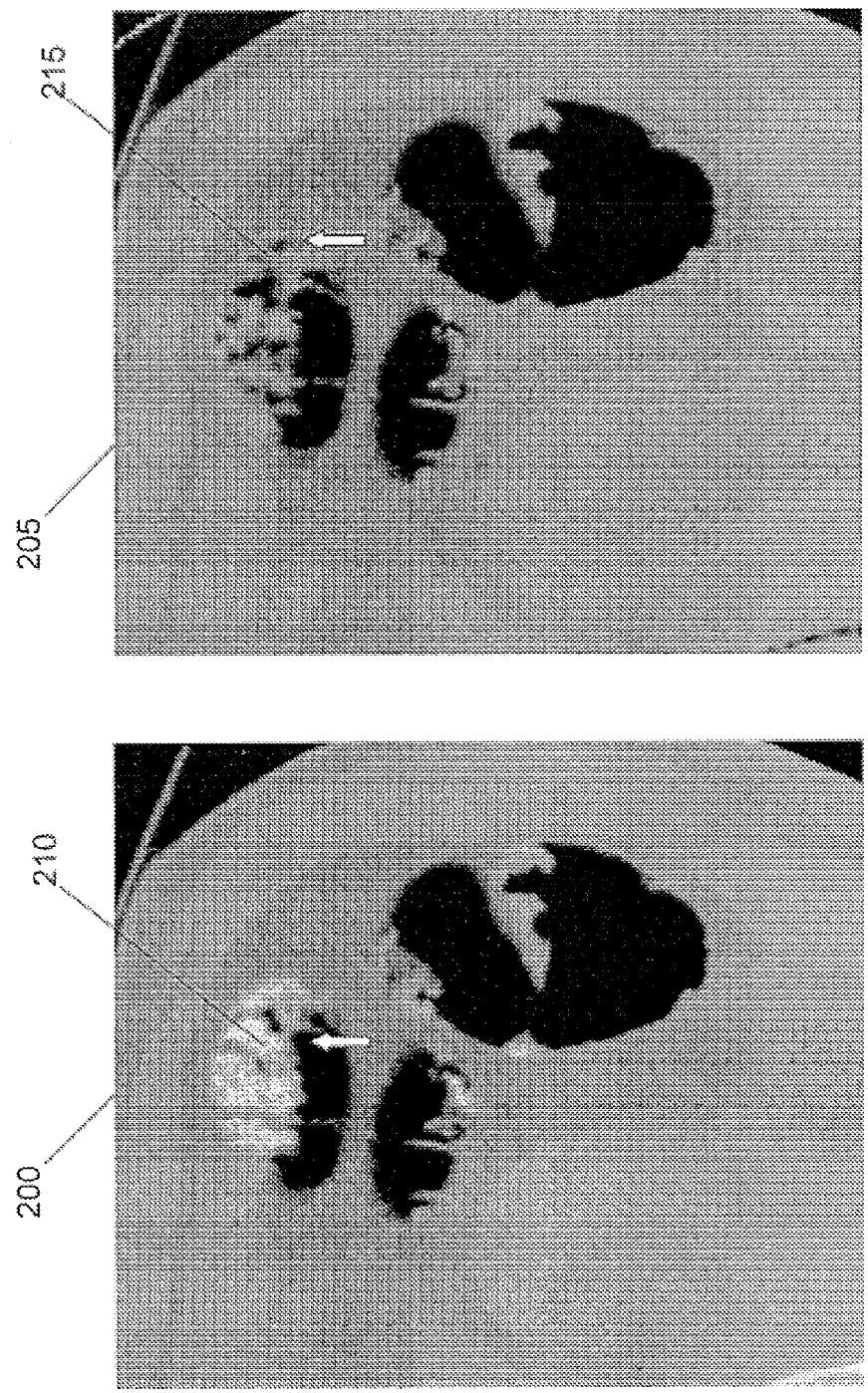
FIG. 2 shows another exemplary CT colonography images resulting from the use of conventional EC techniques to electronically cleanse tagged bowel contents from the images.
Figure 3:
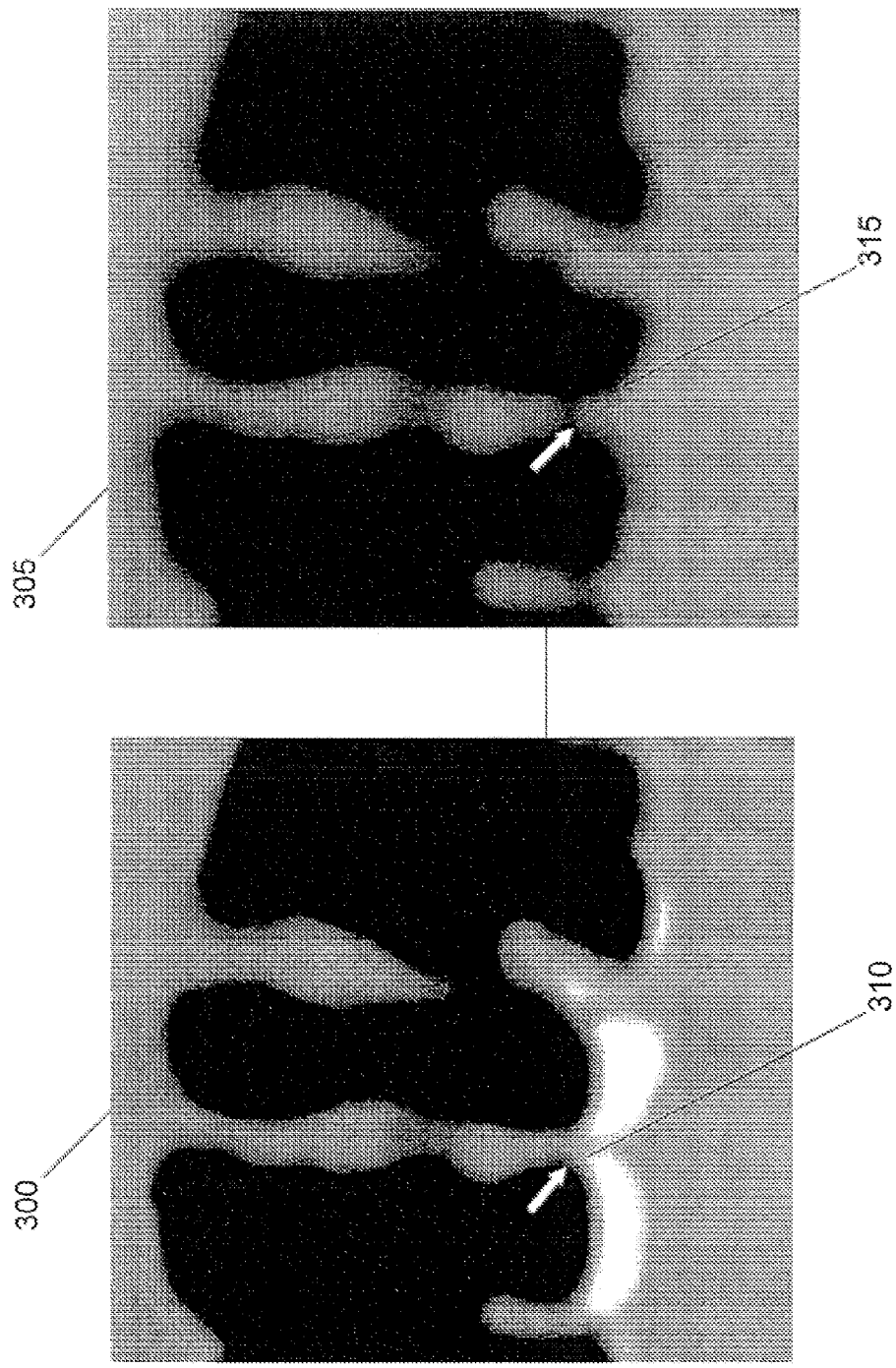
FIG. 3 shows yet another exemplary CT colonography images resulting from the use of conventional EC techniques to electronically cleanse tagged bowel contents from the images.
Figure 4:
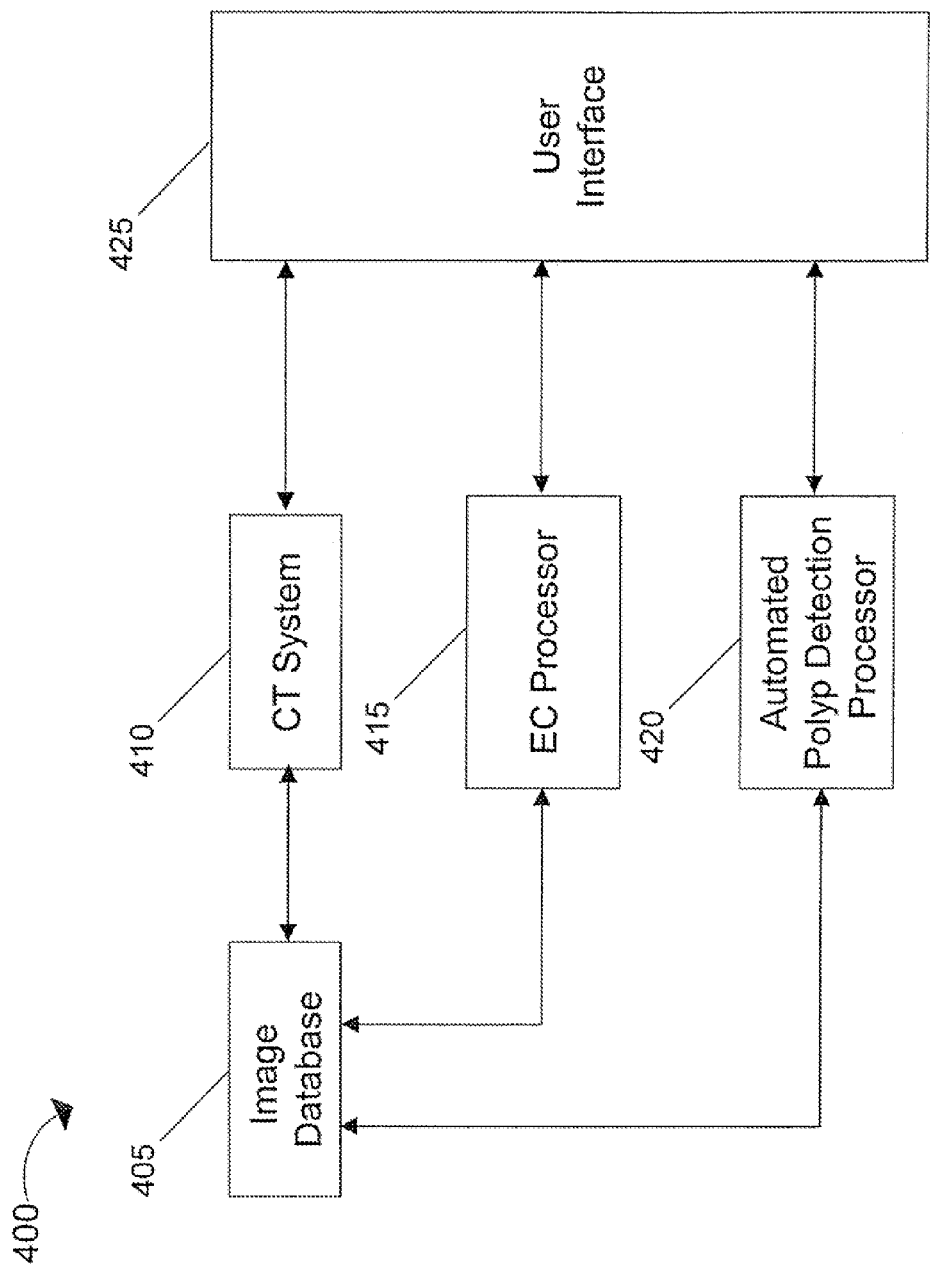
FIG. 4 shows a block diagram of an exemplary embodiment of a system for EC of CT colonography images and automatic polyp detection in accordance with the present invention.

A block diagram of an exemplary embodiment of a system/arrangement 400 according to the present invention for performing EC of the CT colonography images and automatic polyp detection is illustrated in FIG. 4. As shown in FIG. 4, the system 400 for performing a virtual colonoscopy includes a CT system 410 having a storage device, e.g., an image database 405, coupled to the CT system 410. As known to one skilled in the art, the CT system 410 can produce two-dimensional images of cross-sections of regions of the human body by measuring attenuation of X-rays through a cross-section of the body. The images may be stored as digital images or other data in the image database 405. A series of such two-dimensional images can be combined using conventional techniques to provide a three-dimensional image of a patient's colon. A user interface 425 can allow a user, e.g., a medical examiner, to operate the CT system 410 and to access and view the images stored in the image database 405.

An electronic cleansing processor ("ECP") 415 can be coupled to the image database 405 and the user interface 425. The ECP 415 can receive image data from the image database 405 and processes the image data to remove the contents of the patient's bowel from the images. The ECP 415 can then store the processed images with the bowel contents removed into the image database 405. The particular manner in which the ECP 415 processes the images to subtract or remove the bowel contents from the images is described in more detail herein below.

In particular, an EC technique implemented in the ECP 415 for removing bowel contents from images stored in the image database 405 may include, but not limited to: (i) an initial segmentation of colon in the images; (ii) an initial classification of the segmented colon in the images; (iii) computation of local-shape signatures in the images; (iv) detection of soft-tissue structures (polyp and fold) while subtracting the tagged regions in the images; and (v) a mucosa reconstruction. Since the ECP 415 can digitally subtract or otherwise remove the bowel contents from the images using these exemplary steps, which are described in more detail herein below, the patient undergoing the virtual colonoscopy with the virtual colonoscopy system/arrangement 400 does not have to purge the bowel prior to the examination in the conventional manner which is known to be unpleasant to the patient.

An automated polyp detection processor ("APDP") 420 is coupled between the image database 405 and the user interface 425. The APDP 420 receives image data from the image database 405, and processes the image data from the image database 405 to detect and/or identify polyps, tumors, inflammatory processes, or other irregularities in the anatomy of the patient's colon. The APDP 420 can thus pre-screen each image in the image database 405 such that a medical examiner, e.g., a doctor, need not examine every image but rather can focus attention on a subset of the images possibly having polyps or other irregularities. Since the CT system 410 may generate a relatively large number of images for each patient undergoing a virtual colonoscopy with virtual colonoscopy system/arrangement 400, the medical examiner can be provided with additional time to focus on those images in which the APDP 420 is most likely to detect a polyp or other irregularity in the colon.

Exemplary embodiments of a APDP 420 in accordance with the present invention are described in U.S. Pat. No. 6,497,784 and U.S. Publication No. 2005/0107691, the disclosures of which are incorporated herein by reference in their entirety. It should be understood by those of ordinary skill in the art that the APDP 420 can process images which have been generated using either conventional virtual colonoscopy techniques, e.g., techniques in which the patient purges the bowel prior to the CT scan, or images in which the bowel contents have been digitally removed, e.g., images which have been generated by the ECP 415.

Figure 5:
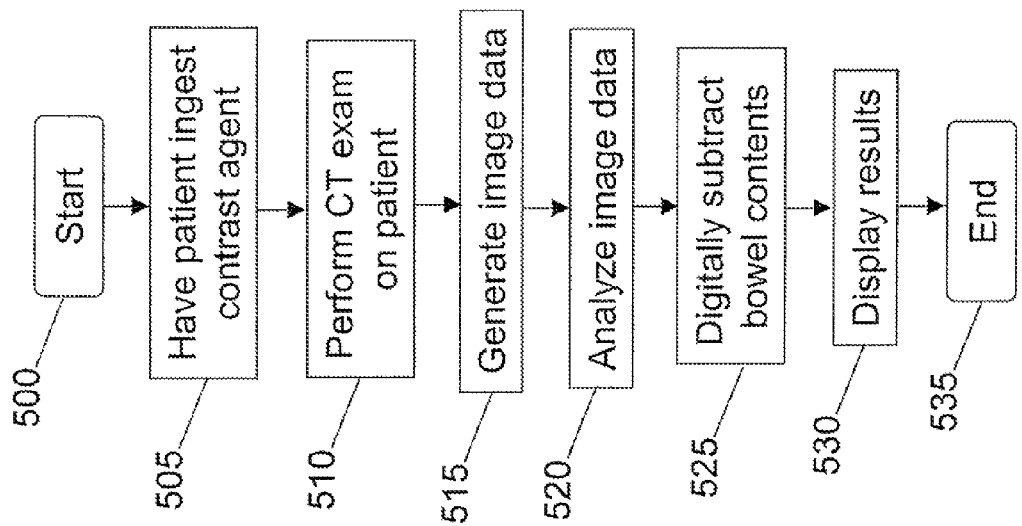
FIG. 5 shows a flow diagram of an exemplary embodiment of a virtual colonoscopy procedure performed in accordance with the present invention.

Referring to FIG. 5, a flow diagram of an exemplary embodiment of a virtual colonoscopy procedure performed in accordance with the present invention is provided. A virtual colonoscopy examination conducted on the patient using the exemplary virtual colonoscopy system/arrangement 400 of FIG. 4 may start in step 505 by placing a contrast agent in the region of the patient's colon to be examined. Typically, the patient can ingest the contrast agent to mark or tag the bowel contents. It should be appreciated, however, that any technique for placing the contrast agent in the bowel may also be used. The contrast agent may be taken in small amounts with meals beginning approximately 48 hours or so prior to a scheduled exam. The contrast agent can be of any of the commercially available types such as Gastrogratfin, Barium, or Oxilan, for example.

Further, as shown in step 510, the CT exam takes place, and images of a body region, e.g., an entire abdomen, can be generated (step 515). The image data is then transmitted to an analysis system, and analyzed (step 520). One or more images may be selected for analysis, e.g., a single slice or series of slices. This can be accomplished by using commercially available systems such as the Vitrea System available through Vital Images, Inc., of Minneapolis, Minn.

Then, as shown in step 525, the contents of the patient's bowel may be digitally subtracted from the CT images using the ECP 415 shown in FIG. 4, as described in more detail herein below. After the digital subtraction procedure is performed using the ECP 415, the processed images may be stored back into the image database 405. The results of the images having the bowel contents thereof digitally removed may then be displayed (step 530).

Figure 6A:
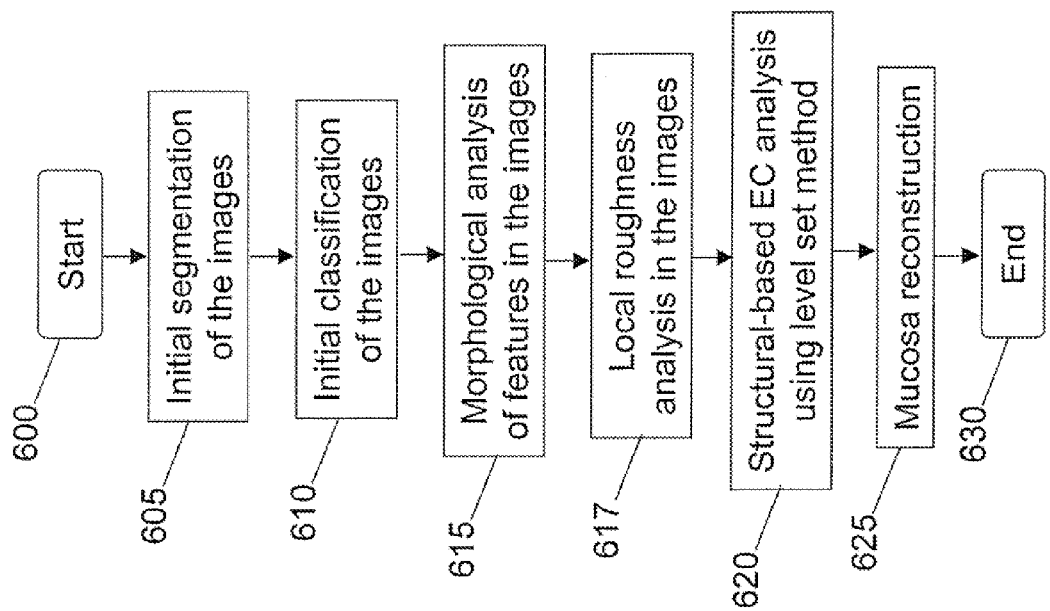
FIG. 6A shows a flow diagram of an exemplary embodiment of a procedure according to the present invention for performing EC of CT colonography images.

Referring to FIG. 6A, a flow diagram of an exemplary embodiment of a procedure according to the present invention for performing EC of CT colonography images is provided. The ECP 415 shown in FIG. 4 can remove bowel contents from CT colonography images by performing the following: (i) an initial segmentation of the colon in the images (step 605), (ii) an initial classification of the segmented colon in the images (step 610), (iii) a morphological analysis of features in the images (step 615), (iv) a local roughness analysis in the images (step 617), (v) a structural-based EC analysis using a level set method on the images (step 620), and) mucosa reconstruction (step 625). As another exemplary embodiment of the present invention, steps 615-620 can be replaced and/or include with a computation of local shape signatures in the image and followed by a structure EC analysis using a morphological information.

For example, in step 605, the ECP 415 segments the colon in the CT images, which includes: (i) colonic wall, (ii) colonic lumen, and (iii) tagged bowel contents. The segmentation may be performed by using a combination of well-known techniques including thresholding, connectivity, morphological operators, and texture features, such as standard deviation, local histogram, entropy, and energy, among others. Exemplary thresholding techniques for segmenting colon in CT images above include the techniques described in U.S. Pat. No. 6,947,784 and U.S. Patent Publication No. 2005/0107691.

Further, in step 610, the ECP 415 classifies each voxel in the segmented CT images into a number of (e.g., three) different materials: (i) air, (ii) soft tissues, and (iii) tagged bowel contents. Similarly to the image segmentation step 605, the image classification step may be performed using thresholding, connectivity and morphological operators. Further characterization of tagged bowel contents may be made using local three-dimensional texture analysis, which is dependent on calculation of standard deviation of voxels in a kernel surrounding a voxel in question. Tagged bowel contents, which may contain air admixed with water, may lead to an increased standard deviation. In this classification method, a kernel may be first scanned through the voxels previously characterized as soft tissues using thresholding. Certain regions demonstrating high standard deviations may then be reclassified as tagged bowel contents.

Along borders between soft tissue and air, i.e., along the colonic mucosa, the symmetry of regions in the statistical kernel may be used to further limit the reclassification, as follows: tagged bowel contents are generally uniformly variable, whereas when soft tissue abuts air (such as in the colonic mucosa), the variability tends to be limited in the appropriate kernel. For example, sub-regional standard deviations in the kernel may be low, especially at the corners of the kernel. This may not be the case with tagged bowel contents, which tend to have a uniformly high standard deviation throughout all regions of the kernel.

Figure 6B:
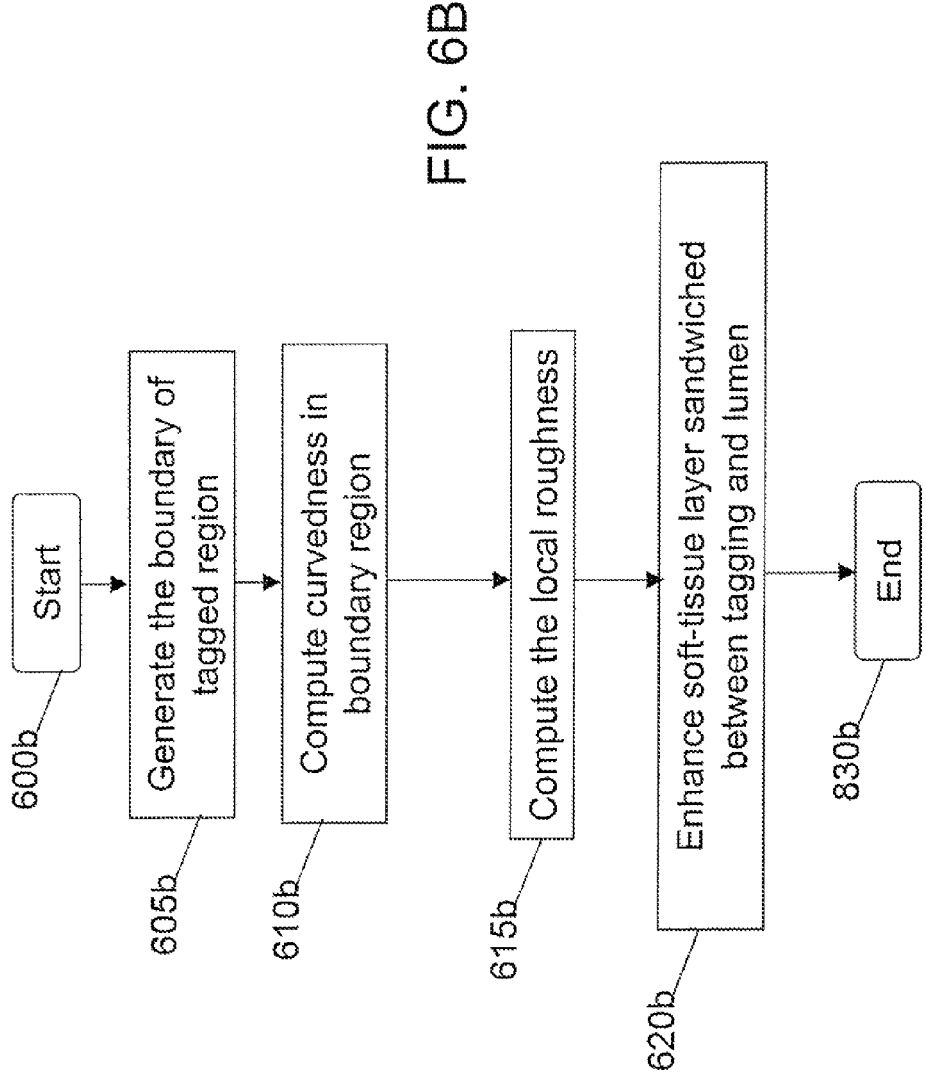
FIG. 6B shows a flow diagram of an exemplary embodiment of details of a procedure according to the present invention for performing a roughness determination indicated in the procedure of FIG. 6A.

Upon classifying each voxel into either air, soft tissue, or tagged bowel content in step 610, a morphological classification of features in the segmented CT images can be performed in step 615 and a local roughness analysis can be done in step 617. Details of steps 615 and 617 of FIG. 6A are illustrated in FIG. 6B. For example, the local roughness of the image can be assessed to determine whether a voxel is on a lumen-tissue boundary or on a thin soft-tissue structure provided between tagged matter and air. This exemplary procedure is based on an observation that a surface generated by an L-T boundary is often more irregular than that of soft-tissue structures because of the local non-linear volume averaging caused by PVE on the interface situated between the tagged region and air.

For example, such surface irregularity can be reduced when a thin soft-tissue structure is located in the middle of the tagged region and air because of the smoothness of the surface of soft-tissue structures. Generally, the iso-surface on the L-T boundaries can often be disconnected, whereas that of thin soft-tissue structures is likely connected and smooth. This may indicate that the L-T boundary is more irregular than the thin soft-tissue structures sandwiched between tagged regions and the lumen. Thus, the roughness of the local iso-surface can be used to measure the irregularity.

As shown in FIG. 6B, a boundary of the tagged region can be generated in step 605*b*. Then, a curvedness in the boundary region is determined in step 610*b*. Further, a local roughness can be computed based on the curvedness in step 615*b*. In particular, a local roughness at point x can be defined as the cumulative difference of the local generate iso-surface curvedness, $CV_\sigma(x)$, between adjacent scales, as follows:

$$R_{ij} = \sum_{i=1}^{n} (B_i \cdot \Delta CV_i^2), \tag{1}$$

where $\Delta CV_i = CV_{\sigma_i}(x) - CV_{\sigma_{i-1}}(x)$ represents the difference in the curvedness values at scales i and i−1, and $B_i$ is a scale-dependent basis function that weights the difference of the curvedness values at each scale. The local iso-surface curvedness at voxel x can be defined as $$CV_\sigma(x) = \sqrt{\frac{\kappa_{min}^\sigma(x)^2 + \kappa_{max}^\sigma(x)^2}{2}}, \tag{2}$$

where $\kappa_{max}^\sigma$ and $\kappa_{min}^\sigma$ are the minimum and maximum principal curvatures at scale σ (as described in J. J. Koenderink, Solid Shape, Cambridge, Mass.: MIT Press, 1990; and G. Lohmann, Volumetric image analysis, John Wiley & Son Ltd, 1998). The curvedness $CV_\sigma$ can be computed in step 615*b* by, e.g., filtering of the images with an increasing scale, from scale 0 ($\sigma_o$) to scale n ($\sigma_n$), and then, at each scale i, by an application of the first and second derivative filters of size $\sigma_i$ to the image. In step 620*b*, the soft tissue layer provided between the tagged portion and lumen can be enhanced using the above-described information.

The structure-analysis can take into account different local shape signatures of polyps and folds to determine the probability of each voxel in an image being in a polyp or fold region of the image. The probabilities may be determined by using a unique signature analysis of the eigenvalues of a Hessian operator applied to the segmented CT image, as described in more detail herein below with reference to FIG. 8.

The exemplary matrix of probabilities can be used in the structure-based EC analysis as provided step 620 to determine the contour and boundary of regions corresponding to tagged bowel contents so they can be accurately removed from the CT images. The structure-based EC analysis as provided in step 620 a shape-based speed function to accurately identify the regions corresponding to the tagged bowel contents in the CT images. The shape-based speed function can generally act on a given colon surface and at any moment in time, may define a "level-set" partial differential equation ("PDE") which is solved to determine the surface position and hence, its contour and boundary.

In an exemplary embodiment of the present invention, the speed and direction of the shape-based speed function relative to the given colon surface can be determined based on the morphological information in the images, e.g., based on the matrix of probabilities obtained in step. The shape-based speed function can modulate the speed at each point using a threshold-based function, with thresholds determined according to a dynamic histogram analysis, as described in further detail herein below with reference to FIGS. 11A-B. The initial conditions of the PDE can be specified according to the initial segmentation and classification steps 605-610.

After accurately identifying the regions in the CT images corresponding to the tagged bowel contents by performing the structure-based EC analysis in step 615, the tagged bowel contents may be digitally subtracted from the CT images in step 620. The regions corresponding to the removed bowel contents are then replaced with air, and their borders are reconstructed. The images having the tagged bowel contents removed may then be stored back into the image database 405 for display and analysis by the medical examiner.

Morphological Classification of Features

Morphological information in a CT image may be used to classify features in the image such as folds and polyps. In particular, morphological information may help avoid the pseudo-enhancement and inappropriate removal of very thin folds and polyps surrounded by tagged bowel contents.

In one exemplary embodiment of the present invention, morphological information of features in a image may be extracted by analyzing second order derivatives in a region-of-interest ("ROI") in the image. The ROI in an image may be represented by a matrix having a size that corresponds to the size of the ROI and elements that correspond to the voxels in the ROI.

As known to those of ordinary skilled in the art, it is common in image processing to use first order derivatives so as to detect the edges contained within an image. The first order derivatives are generally referred to as the gradient operator, or $\nabla I = (I_x, I_y, I_z)$.

To encode additional information in the image, such as morphological information of features in the image, second order derivatives are generally used. A conventional procedure for analyzing the second order derivatives of the ROI in an image may be the use of the Hessian matrix operator. A Hessian matrix operator, denoted by H, may be given by:

$$H = \begin{vmatrix} I_{xx} & I_{xy} & I_{xz} \\ I_{yx} & I_{yy} & I_{yz} \\ I_{zx} & I_{zy} & I_{zz} \end{vmatrix} \tag{3}$$

where each element corresponds to a second order derivative, e.g., $$I_{xx} = \frac{\partial^2}{\partial x^2} I, I_{xy} = \frac{\partial^2}{\partial x \partial y} I,$$

etc.

Since H is a symmetric matrix, it has three real eigenvalues that are invariant in rotation. The corresponding eigenvectors are generally referred to as "principal directions," and are orthogonal. The eigenvalues and corresponding eigenvectors can be thought of as describing the magnitude and principal directions of pixel variability in the ROI being analyzed. The eigenvalues can be denoted as $\lambda_1$, $\lambda_2$, and $\lambda_3$, with $\lambda_1 \geq \lambda_2 \geq \lambda_3$, and the corresponding eigenvectors can be denoted as $\theta_1$, $\theta_2$, and $\theta_3$, respectively.

Applying the Hessian operator H on a given ROI in an image and analyzing the relationships between the eigenvalues can permit classification of morphological features in the ROI. For example, the Hessian operator H has been previously employed to morphologically classify three anatomic features, as shown in Table 1 below:

TABLE 1

Conventional eigenvalue signatures for morphological classification of anatomic features

| Anatomic Feature | Morphological Classification | Eigenvalue Condition | Decomposed Condition |
|---|---|---|---|
| Cerebral Cortex | Sheet | $\lambda_3 \ll \lambda_2 \cong \lambda_1 = 0$ | $\lambda_3 \ll 0$ and $\lambda_3 \leq \lambda_2 \cong 0$ and $\lambda_3 \ll \lambda_1 \cong 0$ |
| Vessel | Line | $\lambda_3 \cong \lambda_2 \ll \lambda_1 = 0$ | $\lambda_3 \ll 0$ and $\lambda_3 \cong \lambda_2$ and $\lambda_2 \ll \lambda_1 \cong 0$ |
| Nodule | Blob | $\lambda_3 \cong \lambda_2 \cong \lambda_1 \ll 0$ | $\lambda_3 \ll 0$ and $\lambda_3 \cong \lambda_2$ and $\lambda_2 \cong \lambda_1$ |

As shown in Table 1, each anatomic feature is given a morphological classification according to an eigenvalue condition or eigenvalue signature. That is, if the eigenvalues of the Hessian operator H satisfy a given condition for a given ROI, with the condition corresponding to a known eigenvalue signature of a given morphological feature, the pixels within the ROI will be characterized as belonging to that morphological feature, i.e., the ROI will be deemed to be a part of the region encompassing the morphological feature in the image.

Eigenvalue signatures have conventionally been used to augment the segmentation of vascular structures in medical images (see, for example, Sato et al., "3D Multi-Scale Line Filter for Segmentation and Visualization of Curvilinear Structures in Medical Images," *Medical Image Analysis*, Vol. 2, pp. 143-168, 1998, and Frangi et al., "Mutiscale Vessel Enhancement Filtering," *Lecture Notes in Computer Science*, 1496:130-137, 1998), the entire disclosure of which is incorporated herein by reference. This approach exploits the fact that vascular structures are tubular in shape.

In one exemplary embodiment according to the present invention, eigenvalue signatures may also be used to improve the identification of polyps and folds in CT colonography images. Using the Hessian operator H on a ROI that iteratively moves throughout an image, polyps can be identified as bi-convex features and folds can be identified as convex rims arising from the colon mucosa. In particular, a fold can be identified with the following eigenvalue signature generally corresponding to an arc:

$$\lambda_1 \gg 0 \text{ and } \lambda_3 \ll \lambda_1 \text{ and } \lambda_3 \ll \lambda_2 \cong 0 \quad (4)$$

For polyps, the following eigenvalue signature may be used:

$$\lambda_1 \gg 0 \text{ and } \lambda_3 \ll \lambda_1, \text{ and } \lambda_3 \ll \lambda_2 \ll 0 \quad (5)$$

The eigenvalue signatures corresponding to folds and polyps can be used to enhance them prior to removal of tagged bowel contents. This may prevent an inappropriate removal of the identified folds and polyps, in particular, those very thin folds surrounded by tagged bowel contents. In one exemplary embodiment, the following function may be applied to the folds identified with the eigenvalue signature of Equation (4) above to enhance them prior to removal of the tagged bowel constants:

$$\text{Fold}=\text{Linear}(\lambda_3,\lambda_1)\cdot\text{Arch}(\lambda_1,\lambda_2) \quad (6)$$

where Linear and Arch refer to linear dependent function and arch is an arch shape dependent function.

Figure 7:
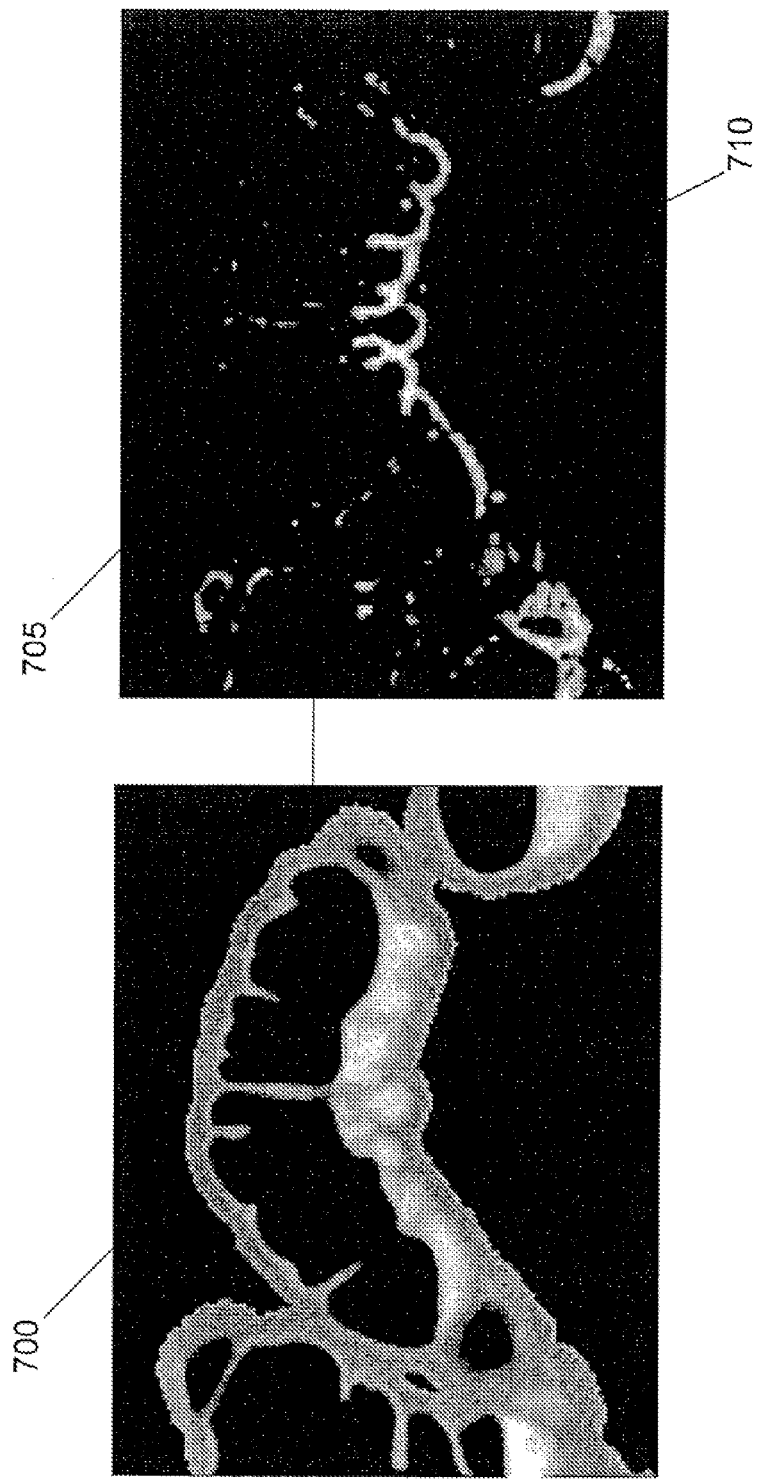
FIG. 7 shows exemplary CT colonography images generated before and after an enhancement of folds that are identified via an analysis of local shape signatures in the images in accordance with the present invention.

Applying the above Equation (6) to enhance folds allows folds submerged in tagged bowel contents to be preserved in the exemplary CT image, as shown in FIG. 7. The CT colonography image 705 of FIG. 7 shows folds 710 after the enhancement procedure has been utilized. The folds 710 were partially submerged in tagged bowel contents, as shown in CT colonography image 700. Their enhancement allows for their preservation during the removal of the tagged bowel contents.

The morphological classification of features using eigenvalue signatures may be used to modulate the speed of a shape-based speed function, as described in more detail herein below. To do so, a matrix of probabilities can be generated to attach to each voxel in a image, a probability that the voxel belongs to a morphological feature classified using eigenvalue signatures, i.e., the probability that the voxel is part of a fold or polyp.

Figure 8:
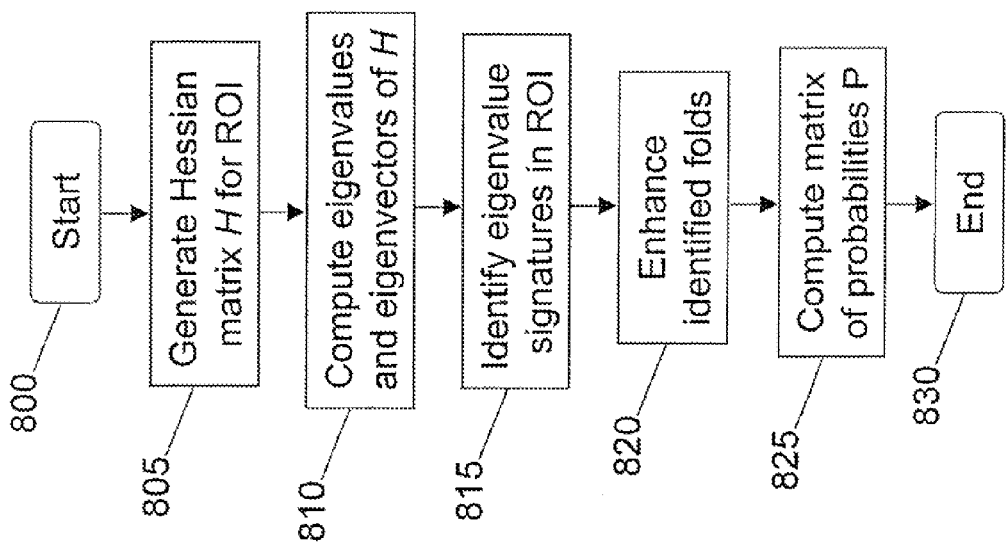
FIG. 8 shows a flow diagram of an exemplary embodiment of a procedure according to the present invention for generating a matrix of probabilities for a particular region of interest ("ROI") based on an analysis of local shape signatures in the CT colonography images.

Referring to FIG. 8, a flow diagram of an exemplary embodiment of a procedure according to the present invention for generating a matrix of probabilities for a given ROI based on a morphological classification of features in the CT colonography images is provided. For example, in step 805, the Hessian matrix H can be constructed for the given ROI. Further, in step 810, the eigenvalues and eigenvectors of H are determined or computed. Eigenvalue signatures are then applied to the ROI to identify morphological features in the ROI (step 815). In step 820, identified folds, if any, are enhanced. In addition, a matrix of probabilities P is generated for the ROI in step 825. The matrix of probabilities P can be used to modulate a shape-based speed function, as described in more detail herein below.

Shape-Based Speed Function

A shape-based speed function may be used to accurately identify the contour and boundary of regions in the CT colonography images corresponding to tagged bowel contents. Speed functions can generally be used in the level-set approach to boundary analysis, described originally in Osher et al., "Fronts Propagating with Curvature-Dependent Speed: Algorithms Based on Hamilton-Jacobi Formulations," *Journal of Computational Physics*, 79, pp. 12-49, 1988, the entire disclosure of which is incorporated herein by reference. The level-set approach uses the framework of partial differential equations ("PDEs") to move one surface against another in order to compute surface boundaries.

In this exemplary framework, the motion or propagation of a surface may be controlled by a set of speed functions, which generally act on the surface and at any moment in time, can define a "level-set" PDE that is solved to find the surface position and hence, its contour and boundary. A speed function can be defined in numerous ways, depending on the application (see, for example, Sethian, J., Level Set Methods: Evolving Interfaces in Geometry, Fluid Mechanics, Computer Vision and Material Sciences, Cambridge University Press, 1996, the entire disclosure of which is incorporated herein by reference).

The level-set approach to boundary analysis can be mathematically explained as a n-dimensional surface embedded in a $R^{N+1}$ space. A scalar function, denoted by $\phi(x,t)$, defines an embedding of a surface S, where $x \in R^{N+1}$ and t is time. The set of points on the surface S can be mapped by $\phi$ such that:

$$S = \{x | \phi(x) = k\} \quad (7)$$

where k is an arbitrary scalar value (often zero, for a zero level-set).

Figure 9A:
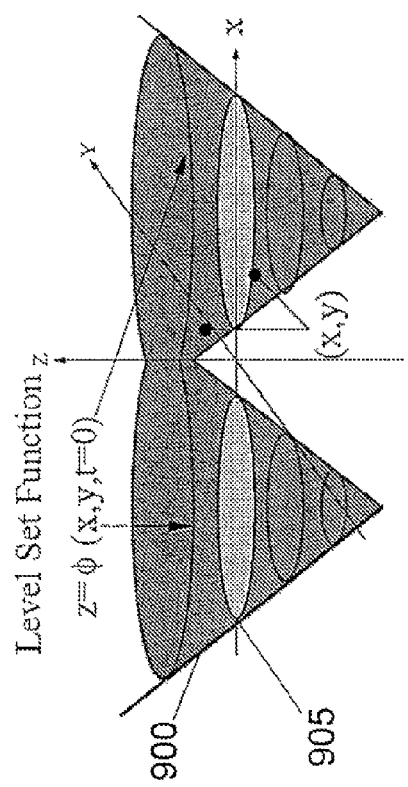
FIGS. 9A and 9B show illustrations of an exemplary level set representations for a use in a shape-based speed function in accordance with the present invention.
Figure 9B:
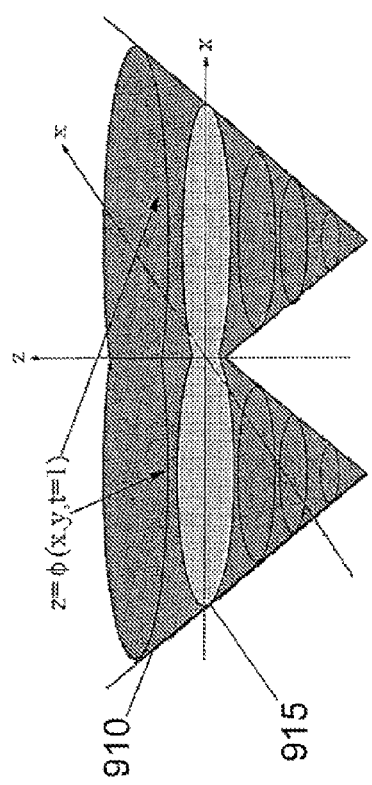

An exemplary level-set representations for embedding a two-dimensional surface according to the present invention in a three dimensional space is illustrated in FIGS. 9A and 9B. The level-set surface 900 plots the distance from each point (x,y) in the surface to the interface 905 of FIG. 9A. A speed function F may be used at each point in time to yield a new interface. For example, a new interface 915 of FIG. 9B is generated at time t=1 while the interface 905 is generated at time t=0. Propagating the level-set over time yields the accurate contour and boundary of the surface 900.

To propagate $\phi$ in time, the following first-order PDE may be defined:

$$\frac{\partial \phi}{\partial t} = F |\nabla \phi| \quad (8)$$

where F is a signed speed function that defines the speed in the direction normal to $\phi$ at any point. F may take a variety of forms (depending on the application) to maximize the desired properties of the final surface boundaries.

When F has been established, the level-set and the resolving interface of 0 can be updated according to the following PDE:

$$\phi(x, t+\Delta t) = \phi(x, t) + \Delta t F |\nabla \phi| \quad (9)$$

The mean curvature of $\phi$, or referred simply as curvature, is commonly used as a speed function to propagate $\phi$. A curvature speed function is often used as a smoothness constraint and combined with other speed functions to smooth out an otherwise rough surface solution. The up-wind scheme (see Osher et al., "Fronts Propagating with Curvature-Dependent Speed: Algorithms Based on Hamilton-Jacobi Formulations," *Journal of Computational Physics*, 79, pp. 12-49, 1988, the entire disclosure of which is incorporated herein by reference) may be used to approximate the first-order differences of the PDE in Equation (9) above to avoid the overshooting associated with finite forward differences.

Because level-set procedures embed a surface in a space that is one-dimensionally higher, the increase in dimension leads to more computationally complexity. However, a single level-set, such as the zero level-set, narrow-band (see Adalsteinsson et al., "A Fast Level Set Method for Propagating Interfaces," *J. Comp. Physics*, 118, pp. 269-277, 1995, the entire disclosure of which is incorporated herein by reference) and sparse-field approaches (Whitaker, R., "A Level Set Approach to 3D Reconstruction from Range Date," International Journal of Computer Vision, 29(3), pp. 203-231, 1998, the entire disclosure of which is incorporated herein by reference) are likely more efficient to solve evolving equations in the area of the surface (interface) rather than the size of $R^{N-1}$ space.

Level-set procedures have been conventionally applied to improve the segmentation of vascular structures in MRI images (see, for example, Suri et al., "Shape Recovery Algorithms Using Level Sets in 2D/3D Medical Imagery: a State-of-the-Art Review," *IEEE Trans. Inf. Technol. Biomed.*, 6(1): 8-28, March 2002, the entire disclosure of which is incorporated herein by reference). Presently, however, it is unknown if the level-set procedures applied specifically to the segmentation of colonic structures.

According to one exemplary embodiment of the present invention, a level-set procedure is provided to perform EC of the CT colonography images. Referring to FIG. 10, a flow diagram of an exemplary embodiment of such procedure according to the present invention for performing a structure-analysis EC using morphological classification of features from the CT colonography images is provided.

For example, in step 1005, a level-set scalar function, denoted by $\phi(x,t)$, is defined according to Equation (7) above. Further, in step 1010, a shape-based speed function F that modulates the speed of propagation of the level-set function $\phi$ is specified. The shape-based speed function F modulates the speed of propagation using the difference between a dynamic threshold T and the probability that a particular voxel x belongs to a morphological feature classified using eigenvalue signatures, i.e., the probability P(x) that the voxel x is part of a fold or polyp, as described herein above with reference to FIG. 8. The shape-based speed function F may be given by:

$$F(x) = \text{sign}(x) \cdot \alpha \cdot |x|^n \quad (10)$$

where $\alpha$ is a scalar, sign(x) is a sign function, n is a factor to control the smoothness of the speed, $$x = \begin{cases} -1; & \text{if } x < \text{threshold} - \text{range} \\ \frac{P(x) - \text{threshold}}{\text{range}} & \text{if } \text{threshold} - \text{range} < x < \text{threshold} + \text{range} \\ 1; & \text{if } x > \text{threshold} + \text{range} \end{cases} \quad (11)$$

e.g., n=2 or 3, and x is the normalized difference given by:

Equation (11) is preferably the speed function to drive the level-set front moving. The probability can be a real value between 0 and 1. For example, if a voxel has a fold-shape probability which is above the probability threshold (such as, e.g., 0.8), then it is possible to treat it as a fold.

The variables T and range can be determined based on a dynamic histogram analysis described herein below with reference to FIGS. 11A and 11B.

The speed function F may need to be balanced with other smoothness constraints, mean curvature, plus an additional uniform smoothing to the level-set function $\phi$. Additionally, in step 1015, the level-set function $\phi$ is propagated to find the boundary of regions corresponding to tagged bowel contents so they can be appropriately removed. The propagation of $\phi$ is performed by solving the following PDE:

$$\frac{\partial \phi}{\partial t} = F_{threshold}(x) |\nabla \phi| + C_{curvature} \nabla \cdot \left( \frac{\nabla \phi}{\nabla_I} \right) |\nabla \phi| + C_{SM} \nabla^2 \phi \quad (12)$$

After solving the PDE in Equation (12) above and determining the boundary of regions corresponding to tagged bowel contents, the tagged bowel contents can be removed and their regions are replaced with air (step 1020). The colonic walls can then be reconstructed, and the CT image may be inserted back in image database 405 by the ECP 415 of FIG. 4.

Dynamic Histogram Analysis

A dynamic histogram analysis can be performed on the CT image to determine the proper threshold T and the range for the speed function F described herein above. Histogram analysis can provide a more flexible method to establish the boundary between objects with different attenuation levels. As a simplified example, if an image consists of an object A and a background B, each with a distinct mean pixel value or attenuation, the histogram of attenuation in the image would likely have two corresponding peaks. Ideally, the boundary between A and B can be selected to identify the valley between these peaks.

In general, an adequate boundary can be established by exemplary threshold procedures if the image histogram peaks are tall, narrow, symmetric, and separated by deep valleys. In practice, the shape of the histogram is generally affected by the relative sizes of the objects in the image, the variance of the pixel values in each object, the number of objects in the image, and the gap between each pair of objects. Because of these effects, the valley of the histogram may not always correspond to what is obtained by using a threshold. This phenomenon is called "threshold bias," and can result in a shifting of the valley (the estimated boundary) toward the smaller object.

The problem of threshold bias in boundary estimation has been addressed in Kittler et al., "Minimum Error Thresholding," *Pattern Recognition,* 19:41-47, 1986, the entire disclosure of which is incorporated herein by reference, by assuming a Gaussian distribution of attenuation for the two object problem. In this exemplary approach, the optimal boundary between objects is calculated based on the minimum of error to fit the Gaussian curve. Other procedures for boundary estimation have included a minimization of the intra-object-class variance, maximization of the inter-object-class variance, and maximization of the image entropy.

These exemplary procedures, however, attempt to adjust bias in a static histogram that includes all objects in the image data. In practice, an estimation of bias using this framework is still difficult, because the histogram is frequently unimodal.

To limit threshold bias, a dynamic histogram analysis approach that employs a moving region of analysis at the boundary of interest may be employed. The region of analysis can be iteratively moved, permitting control over the fraction of the object and its background that are subsumed in the area of analysis. As a result, the histogram observed in the moving region retains the salient valley and peak features that facilitate accurate boundary estimation. In a two dimensional example, if boundary analysis is limited to a region that includes only two features, A (an object) and B (its background) and the size ratio of these two features in the region of analysis, generally referred to as the Background-to-Foreground ("BtF") ratio, is $$T = \frac{M_B + M_A}{2} + \Delta Th, \Delta Th = -\sigma^2 \cdot f \cdot \ln(C_R) \quad (13)$$

approximately one, the threshold bias may be minimized, at a position T, according to:

where $M_A$ and $M_B$ are the expected attenuation values of object A and background B, respectively, $\sigma^2$ is the variance of the observed white noise distribution, f is a scale factor of the two expected attenuation values and given by $$f = \frac{1.0}{M_B - M_A},$$

and $C_r$ is the BtF ratio and given by $$C_r = \frac{R_B}{R_A},$$

with $R_A$ and $R_B$ being the number of voxels of two materials.

The above Equation 13 generally uses a two object limit and a near unitary BtF. These two possible requirements can be met if the two-dimensional region of analysis takes the form of a band.

FIG. 11A shows an illustration of an exemplary band 1100 around an object boundary is shown which is formed with dynamic histogram analysis in accordance with an exemplary embodiment of the present invention. The band 1100 is situated near the boundary between object A and background B. The band 1100 consists of three components: an inner part, an outer part, and a boundary (the medial axis) that separates the two. The band 1100 can be mobile, and its iterative motion may be controlled by a signed speed function. For example, when positive, this function drives the points on the boundary outward, and when negative, the function drives the points inward.

For the description below, it can be assumed that the object A has a higher mean attenuation than the background, i.e., $M_A > M_B$. If the band 1100 is initially positioned so that its boundary lies just within object A, the BtF would be less than 1 because the ratio of subsumed areas in the band will be shifted toward object A. The estimated threshold from the histogram of the band will initially be shifted toward the background. The difference between the observed attenuation along the boundary and the estimated threshold at the boundary defines the scalar 'speed' by which to iteratively propagate the boundary points outward, away from object A. As the band expands, it subsumes more background pixels, bringing the BtF closer to 1. As the BtF ratio of the band approaches 1, the difference between the boundary and the estimated threshold decreases, causing the propagation speed of the shell to converge to zero. The resulting, final position of the boundary is taken as the bias-minimized delimiter between object A and its background.

The dynamic histogram resulting from the propagation of the band 1100 is shown in an exemplary graph 1105 provided in FIG. 11B. The threshold T for use in the speed function F given in Equations 10 and 11 above is provided as the midpoint of the graph 1105, while the range is provided as the range between the two peaks in the graph 1105.

The example described above is provided in two-dimensions which can be extended to three dimensions, such that instead of a band, the propagating region of analysis can become an expanding shell.

Experimental Results

Applying the structure-analysis and the dynamic histogram analysis in a shape-based speed function enables tagged bowel contents to be accurately removed from CT colonography images, thereby facilitating virtual colonoscopy exams to be easily performed on patients without the need for thorough patient preparation.

Figure 12A:
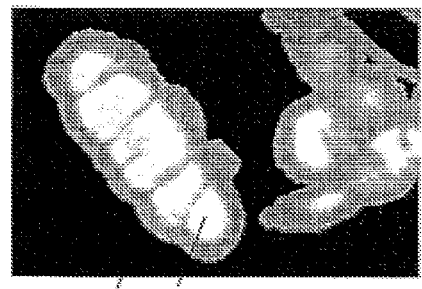
FIGS. 12A-12E show exemplary CT colonography images acquired for a particular subject using the EC performed according to the exemplary embodiment of the present invention.
Figure 12B:
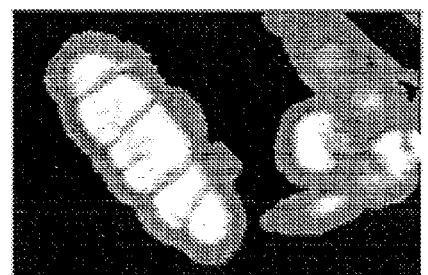

Referring to FIGS. 12A-12E, exemplary CT colonography images acquired for a subject with EC performed according to the present invention are provided. The image 1200, as shown in FIG. 12A, represents a CT colonography image acquired after tagging of the bowel contents 1205. The image 1200 is segmented in step 605 of FIG. 6A, and a initial classification of the image 1200 into air, soft tissues, and tagged bowel contents can be performed in step 610 of FIG. 6A, such resulting in the generation of an image of soft tissues 1215-1220 in image 1210 shown in FIG. 12B.

After the initial classification is performed in step 610, according to a particular exemplary embodiment of the present invention, the CT image 1210 can undergo a morphological classification of its features in step 615 of FIG. 6A. A shape-based EC of the CT image 1210 is then performed in step 620 of FIG. 6 as described hereinabove, resulting in the enhancement of folds 1230 seen in the image 1225, shown in FIG. 12C. The tagged bowel contents are then removed, as shown in the voxel 1240 in the image 1235, shown in FIG. 12D, and the colonic walls are reconstructed in step 625 of FIG. 6A, resulting in the image 1245, shown in FIG. 12E.

Figure 12C:
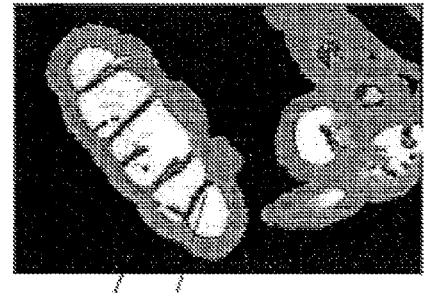
Figure 12D:
Figure 12E:
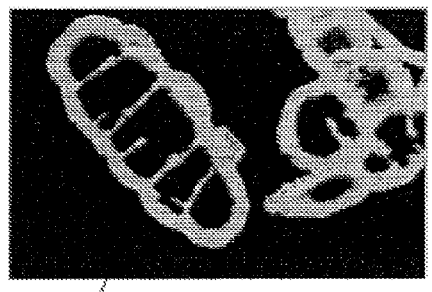

As provided in the image 1245, the tagged bowel contents 1205 were accurately removed, without resulting in the degradation of folds, such as folds 1230 seen in the image 1225 of FIG. 12C. Performing the above-described procedures for the CT colonography images enables virtual colonoscopy to be accurately and easily performed without the need for thorough patient preparation.

Figure 13B:
FIGS. 13A-13D shows exemplary CT colonography images for indicating an exemplary relationship between roughness and boundary in accordance with exemplary embodiments of the present invention.
Figure 13D:
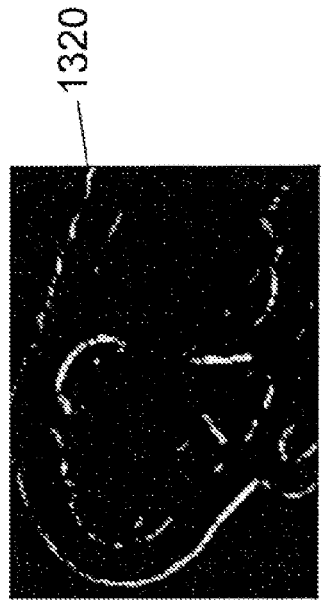
Figure 13A:
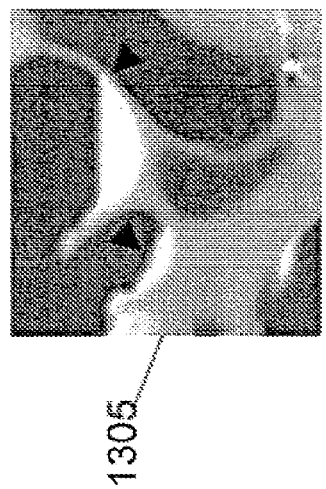
Figure 13C:

FIGS. 13A-13D show exemplary images to indicate the relationship between roughness and the L-T boundary which can be obtained using the exemplary procedure of FIG. 6B. When an image 1305 of FIG. 13A and an image 1310 of FIG. 13B are compare with an image 1315 of FIG. 13C and an image 1320 of FIG. 13D, respectively, thin folds that are buried underneath the tagged objects (see white arrows in the drawing) are generally enhanced, whereas the L-T boundaries (see black arrows in the drawings), especially those of the tagged stools against gravity (see, e.g., a black arrow in the image 1310 of FIG. 13B), are de-enhanced.

The foregoing descriptions of specific embodiments and best mode of the present invention have been presented for purposes of illustration and description only. They are not intended to be exhaustive or to limit the invention to the precise forms disclosed. Specific features of the invention are shown in some drawings and not in others, for purposes of convenience only, and any feature may be combined with other features in accordance with the invention. Steps of the described processes may be reordered or combined, and other steps may be included. The embodiments were chosen and described in order to best explain the principles of the invention and its practical application, to thereby enable others skilled in the art to best utilize the invention and various embodiments with various modifications as are suited to the particular use contemplated. Further variations of the invention will be apparent to one skilled in the art in light of this disclosure and such variations are intended to fall within the scope of the appended claims and their equivalents. The publications referenced above are incorporated herein by reference in their entireties.

What is claimed is:

1. A structure-analysis method configured for providing imaging information with respect to a patient obtained during a virtual colonoscopy, comprising:
   a) generating as part of, or following a virtual colonoscopy, at least one colonography image of at least one region of interest of the patient, the at least one generated colonography image comprising tagged bowel contents of at least one portion of a colon of the patient; and
   b) classifying one or more morphological features in the at least one generated colonography image as at least one of a polyp or a fold;
   c) while at least subtracting or removing, either digitally or electronically, the tagged bowel contents from the at least one generated colonography image, based on the morphological classification, either during or following the classifying step, in order to provide the imaging information, with respect to the patient, as a reconstructed, displayed, and/or stored image.

2. The structure-analysis method of claim 1, wherein the bowel contents of the patient's colon are tagged by having the patient ingest a contrast agent.

3. The structure-analysis method of claim 1, further comprising segmenting the at least one generated colonography image or images into regions comprising at least one of a background, a colonic lumen, a colonic wall, or tagged bowel content regions.

4. The structure-analysis method of claim 3, further comprising classifying the segmented regions into component materials comprising at least one of air, soft tissue, or the tagged bowel content regions.

5. The structure-analysis method of claim 1, wherein the classifying procedure comprises applying a Hessian operator in the at least one region of interest in the at least one generated colonography image.

6. The structure-analysis method of claim 5, further comprising determining eigenvalues and eigenvectors of the Hessian operator.

7. The structure-analysis method of claim 6, further comprising identifying one or more eigenvalue signatures corresponding to the one or more morphological features in the region-of-interest.

8. The structure-analysis method of claim 7, further comprising enhancing one or more folds in the region-of-interest, the folds being identified with one of the eigenvalue signatures.

9. The structure-analysis method of claim 1, further comprising applying a shape-based speed function to the at least one generated colonography image so as to identify image boundaries of regions corresponding to the tagged bowel contents in the at least one generated colonography image before performing step c) the of the structural analysis method.

10. The structure-analysis method of claim 9, wherein the shape-based speed function comprises a thresholding speed function based on the morphological classification.

11. The structure-analysis method of claim 10, wherein the shape-based speed function is controlled by both a threshold and a range.

12. The structure-analysis method of claim 11, wherein the threshold and the range are computed by performing a dynamic histogram analysis of each of the generated, at least one colonography images.

13. The structure-analysis method of claim 1, further comprising reconstructing a mucosa of the at least one portion of the colon in the at least one generated colonography image after the performance of step c).

14. A structure-analysis system configured for providing imaging information with respect to a patient obtained during a virtual colonoscopy, comprising:
   a virtual colonoscopy image processing arrangement configured to:
      generate at least one colonography image of at least one region of interest of the patient, the at least one generated colonography image comprising tagged bowel contents of at least one portion of a colon of the patient, and classify one or more morphological features in the at least one generated colonography image as at least one of a polyp or a fold, while at least subtracting or removing, either digitally or electronically, the tagged bowel contents from the at least one generated colonography image based on the morphological classification, either during or following the classification step, in order to provide the imaging information with respect to the patient, as a reconstructed, displayed, and/or stored image.

15. The structure-analysis system of claim 14, further comprising an image database configured to store the at least one generated colonography image.

16. The structure-analysis system of claim 14, further comprising a user interface configured to interact with the processing arrangement.

17. The structure-analysis system of claim 14, further comprising an automated polyp detection processor which is configured to identify polyps.

18. The structure-analysis system of claim 14, wherein the processing arrangement is further configured to segment the at least one generated colonography image, or colonography images, into regions comprising at least one of a background, a colonic lumen, a colonic wall, or tagged bowel content regions.

19. The structure-analysis system of claim 18, wherein the processing arrangement is further configured to classify the regions into component materials comprising at least one of air, soft tissue, or the tagged bowel content regions.

20. The structure-analysis system of claim 14, wherein the morphological features are classified by applying a Hessian operator in the at least one region of interest of the at least one colonography image.

21. The structure-analysis system of claim 20, wherein the Hessian operator comprises a set of eigenvalues and a set of corresponding eigenvectors.

22. The structure-analysis system of claim 21, wherein the set of eigenvalues comprises one or more eigenvalue signatures corresponding to one or more morphological features in the at least one region of interest.

23. The structure-analysis system of claim 22, wherein one of the eigenvalue signatures corresponds to folds.

24. The structure-analysis system of claim 23, wherein the folds are enhanced in the region-of-interest.

25. The structure-analysis system of claim 14, wherein the processing arrangement is further configured to apply a shape-based speed function directly to the at least one generated colonography image so as to identify image boundaries of regions corresponding to the tagged bowel contents in the at least one colonography generated image before performing the subtracting or removing of the tagged bowel contents.

26. The structure-analysis system of claim 25, wherein the shape-based speed function comprises a thresholding speed function based on the morphological classification.

27. The structure-analysis system of claim 25, wherein the shape-based speed function is controlled by both a threshold and a range.

28. The structure-analysis system of claim 27, wherein the threshold and the range are determined by performing a dynamic histogram analysis of each of the generated, at least one colonography images.

29. The structure-analysis system of claim 14, wherein the processing arrangement is further configured to perform a reconstruction of a mucosa of the at least one portion of the colon in the at least one generated colonography image after the tagged bowel contents are subtracted or removed from the at least one generated colonography image.

30. A structure-analysis method configured for providing imaging information with respect to a patient obtained during a virtual colonoscopy, comprising:
a) generating as part of, or following a virtual colonoscopy at least one colonography image of at least one region of interest of the patient, the at least one generated colonography image comprising tagged bowel contents of at least one portion of a colon of the patient;
b) classifying one or more morphological features in the at least one generated colonography image as at least one of a polyp or a fold; and
c) applying a shape-based speed function on at least one portion of the at least one generated colonography image;
d) while at least or removing, either digitally or electronically, the tagged bowel contents from the at least one generated colonography image based on the application of the shape-based speed function and the morphological classification, either during or following the classifying and applying steps, in order to provide the imaging information, with respect to the patient, as a reconstructed, displayed, and/or stored image.

31. The structure-analysis method of claim 30, further comprising segmenting the at least one generated colonography image or colonography images into segmented regions comprising at least one of a background, a colonic lumen, a colonic wall, and tagged bowel content regions.

32. The structure-analysis method of claim 31, further comprising classifying the segmented regions into component materials comprising at least one of air, a soft tissue, and the tagged bowel content regions.

33. The structure-analysis method of claim 30, wherein the shape-based speed function comprises a thresholding speed function based on the morphological classification.

34. The structure-analysis method of claim 33, wherein the shape-based speed function is controlled by both a threshold and a range.

35. The structure-analysis method of claim 34, wherein the threshold and the range are determined by performing a dynamic histogram analysis of each of the at least one generated colonography images.

36. The structure-analysis method of claim 30, further comprising reconstructing the mucosa of the at least one portion of the colon of the patient in the at least one generated colonography image after step d.

37. A structure-analysis system configured for providing imaging information with respect to a patient obtained during a virtual colonoscopy, comprising:
a virtual colonoscopy, image processing arrangement configured for:
generating at least one colonography image of at least one region of interest of the patient, the at least one generated colonography image comprising tagged bowel contents of at least one portion of a colon of the patient,
classifying one or more morphological features in the at least one generated colonography image as at least one of a polyp or a fold, and
applying a shape-based speed function on the at least one generated colonography image;
while at least subtracting or removing, either digitally or electronically, the tagged bowel contents from the at least one generated colonography image based on the application of the shape-based speed function and the morphological classification, either during or following the classifying and applying steps, in order to provide the imaging information with respect to the patient, as a reconstructed, displayed, and/or stored image.

38. The structure-analysis system of claim 37, wherein the processor is further configured for segmenting the at least one generated colonography image, or images, into segmented regions comprising at least one of a background, a colonic lumen, a colonic wall, and tagged bowel content regions.

39. The structure-analysis system of claim 38, wherein the processor is further configured for classifying the segmented regions into component materials comprising at least one of air, a soft tissue, and the tagged bowel content regions.

40. The structure-analysis system of claim 37, wherein the shape-based speed function comprises a thresholding speed function based on the morphological classification.

41. The structure-analysis system of claim 40, wherein the shape-based speed function is controlled by both a threshold and a range.

42. The structure-analysis system of claim 41, wherein the processor is further configured for determining the threshold and the range by performing a dynamic histogram analysis of each of the at least one generated colonography images.

43. The structure-analysis system of claim 37, wherein the processor is further configured for performing a reconstruction of the mucosa of the at least one portion of the colon of the patient, in the at least one generated colonography image, after the subtraction or removal of the tagged bowel contents.

44. A non-transitory computer readable medium having stored thereon computer-executable instructions of electronically cleansing at least one generated colonography image of a patient, the at least one generated colonography image comprising:
   tagged bowel contents of at least one portion of a colon of the patient, wherein when a computer arrangement executes the computer-executable instructions, the computer arrangement is configured to perform structure-analysis procedures comprising:
      generating the at least one colonography image;
      classifying one or more morphological features in the at least one generated colonography image as at least one of a polyp or a fold; and
      applying a shape-based speed function on the at least one generated colonography image; and
      while at least subtracting or removing, either digitally or electronically, the tagged bowel contents from the at least one generated colonography image based on the application of the shape-based speed function and the morphological classification, in order to electronically cleanse the at least one generated colonography image which is then reconstructed, displayed, and/or stored.

45. The non-transitory computer readable medium of claim 44, further comprising an executable instruction module that which, when executed by the computer arrangement, performs an initial segmentation of the at least one colonography image, the initial segmentation being performed in order to segment the at least one generated colonography image into segmented regions comprising at least one of a background, a colonic lumen, a colonic wall, and tagged bowel content regions.

46. The non-transitory computer readable medium of claim 45, further comprising an executable instruction module which, when executed by the computer arrangement, performs an initial classification of the segmented regions into component materials comprising at least one of air, soft tissue, and the tagged bowel content regions.

47. The non-transitory computer readable medium of claim 44, further comprising an executable instruction module which, when executed by the computer arrangement, performs a mucosa reconstruction of the at least one portion of the colon of the patient.

48. A non-transitory computer readable medium which includes a set of instructions in order to electronically cleanse at least one colonography image of a patient, received by an image processing arrangement, the at least one colonography image received by the image processing arrangement, comprising:
   tagged bowel contents of at least one portion of a colon of the patient, wherein, when the image processing arrangement executes the computer-executable instructions, the processing arrangement is configured to perform structure-analysis procedures comprising:
      applying a shape-based speed function onto the at least one colonography image; and
      classifying one or more morphological features in the at least one colonography image as at least one of a polyp or a fold;
      while at least subtracting and removing, either digitally or electronically, the tagged bowel contents from the at least one colonography image based on the morphological classification and the application of the shape-based speed function, in order to electronically cleanse the at least one colonography image; and
      providing the electronically cleansed colonography image as a reconstructed, displayed, and/or stored image.

49. The non-transitory computer readable medium of claim 48, wherein the processing arrangement is further configured to perform an initial segmentation of the at least one generated colonography image, or colonography images, the initial segmentation being performed in order to segment the at least one colonography image into segmented regions comprising at least one of a background, a colonic lumen, a colonic wall, and tagged bowel content regions.

50. The non-transitory computer readable medium of claim 49, wherein the processing arrangement is further configured to perform an initial classification of the segmented regions into component materials comprising at least one of air, a soft tissue, and the tagged bowel content regions.

51. The non-transitory computer readable medium of claim 48, wherein the processing arrangement is further configured to perform a mucosa reconstruction of the at least one portion of the colon of the patient as an additional structure-analysis procedure before providing the reconstructed, displayed, and/or stored electronically cleansed image.

* * * * *